United States Patent [19]

Lagana et al.

[11] 4,327,068
[45] Apr. 27, 1982

[54] METHOD AND THE REUSE OF SEWAGE WATERS OF THE COMBINED UREA-AMMONIA INSTALLATIONS

[75] Inventors: Vincenzo Lagana, Milan; Umberto Zardi, San Donato Milanese, both of Italy

[73] Assignee: Snamprogetti, S.p.A., Milan, Italy

[21] Appl. No.: 234,159

[22] Filed: Feb. 13, 1981

Related U.S. Application Data

[63] Continuation of Ser. No. 162,425, Jun. 24, 1980, abandoned, which is a continuation of Ser. No. 791,331, Apr. 27, 1977, abandoned.

[30] Foreign Application Priority Data

May 14, 1976 [IT] Italy .............................. 23296 A/76

[51] Int. Cl.³ ............................................. C01C 1/04
[52] U.S. Cl. ...................................... 423/359; 564/69
[58] Field of Search ...................... 423/359, 437, 656; 564/69

[56] References Cited

U.S. PATENT DOCUMENTS

3,361,534  1/1968  Johnson et al. .................... 423/656
3,922,222  11/1975  Van Moorsel ................. 260/555 A

OTHER PUBLICATIONS

Olsen, *Unit Processes and Principles of Chemical Engineering*, (1932), pp. 1-3, D. Van Nostrand Co., Inc.
Riegel, *Industrial Chemistry*, Fifth Edition, (1949), Reinhold Publishing Corporation, pp. 255-257.

*Primary Examiner*—O. R. Vertiz
*Assistant Examiner*—Wayne A. Langel
*Attorney, Agent, or Firm*—Morgan, Finnegan, Pine, Foley & Lee

[57] ABSTRACT

A method is disclosed for reusing the processing condensates in a combined plant for the production of ammonia and urea. The condensates are combined into a single stream, filtered to remove the solid substances in suspension, if any, and fed to a boiler for the production of steam while exploiting the sensible heat. Pollution of sewage waters is prevented while obtaining a considerable economy in the running costs.

2 Claims, 1 Drawing Figure

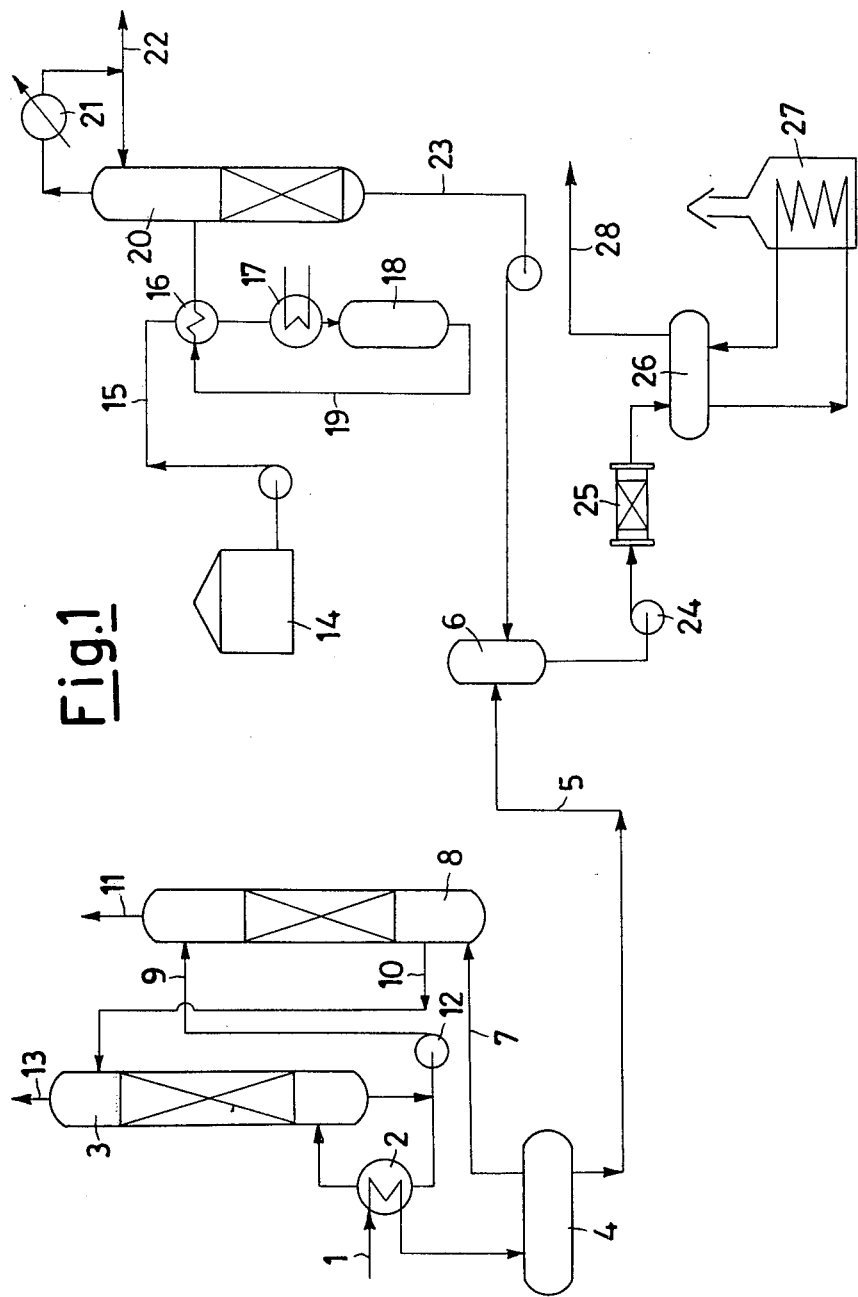

METHOD AND THE REUSE OF SEWAGE WATERS OF THE COMBINED UREA-AMMONIA INSTALLATIONS

This is a continuation application of Ser. No. 162,425 filed June 24, 1980, abandoned, which is a continuation application of Ser. No. 791,331 filed Apr. 27, 1977, abandoned, and which claims the priority of Italian Patent Application No. 23296 A/76 filed on May 14, 1976.

This invention relates to a method for the production of urea in which the sewage waters are reclaimed in a virtually complete way.

It is known that the following main stages are required for the production of urea, viz.:

Production of the hydrogen-nitrogen mixture to be fed to the ammonia production;
Synthesis of ammonia,
Synthesis of urea.

In the first of these main stages, the production of the hydrogen and nitrogen mixture, there is a section for the absorption of carbon dioxide to purify the gas which will then be sent to the ammonia synthesis. Such an absorption section is generally formed by a $CO_2$-absorbing column with a selective solvent and by a regeneration column in which the absorbed $CO_2$ is set free and can be exploited in the installation for the production of urea which is the third of the above enumerated main stages.

According to a few conventional known methods there is used for the regeneration the heat contained in the gas emerging from the preceding CO conversion section prior to feeding said gas to the $CO_2$-absorption stage.

Such a gas contains a high percentage of water, due to the preceding reactions, and which is condensed in the reboiler of the above-mentioned regeneration column from which it is separated and discharged.

An indicative composition of such a condensate is as follows:

| | |
|---|---|
| Ammonia | about 1,000 parts per million |
| Methanol | about 2,000 parts per million |
| Organic substances | about 100 parts per million |
| $CO_2$, $N_2$ and $H_2$ | consistently with the work-temperature and pressure |
| Metals coming from catalysts, refractory bodies, supporting members, etc. | traces |
| Water | the balance to 100% |

Such a condensate can be treated with different methods of a physical nature, such as stripping with air or steam, to reduce the contents of dissolved gases, but its use is at any rate limited by the fact that it is still polluted by polluting substances.

In the stage of urea synthesis, the as-produced waters derive from the reaction as such, in that a mol of water is produced per each mol of product, and also from the condensates as obtained from the vacuum-concentration section of the urea itself.

These waters have, indicatively, a contents of ammonia of about 5% by weight, carbon dioxide of about 2% and urea about 0.1%.

These waters, as a rule, are first treated in a hydrolysis section in which, under appropriate conditions, urea is thermally decomposed into ammonia and carbon dioxide, whereafter the resultant waters are subjected to a physical treatment similar to the one mentioned above for the condensates coming from the decarbonation section, a concentrated phase being thus separated of ammonia and carbon dioxide which can be reclaimed in the urea production plant.

The treated waters find substantially no useful applications in that they have, as an indication, a contents of ammonia and carbon dioxide in the order of magnitude of 40 to 50 parts per million and a contents of urea still in the order of 100 to 200 parts per million.

An object of the present invention is to provide a method for the removal of the processing condensates deriving both from the carbon dioxide absorption installation and from the urea synthesis plant, such method making it possible to suppress the polluting sewage waters as produced by such installations.

The object of the invention is achieved by combining the condensates of the processes coming from the urea synthesis plant and from the carbon dioxide absorption, section, subjecting such condensates to an appropriate filtration so as to remove the solids in suspension, feeding them to a boiler for the production of saturated steam and using the saturated steam as a processing steam in the steam-reforming installation for the preparation of the gas to be fed to the ammonia synthesis plant.

With such a method there is obtained, in the first place, the advantage of eliminating the discharge of polluted waters from the installation, thus solving both the problems of thermal and chemical pollution. Another advantage is inherent in the considerable reduction of the demand of water for the production of steam to be fed to the installation. An additional advantage is then that those process condensates are directly recycled by recovering also the sensible heat thereof and thus reducing the overall heat and power consumptions.

BRIEF DESCRIPTION OF THE DRAWINGS

By way of example and without limitation, FIG. 1 is a diagrammatic illustration of apparatus adapted for use in the practice of our invention.

Through the main 1 the gas coming from the CO-conversion section and essentially composed of nitrogen, hydrogen, carbon dioxide and water, is fed to the reboiler 2 of the regeneration column 3.

In the reboiler 2 a portion of the water contained in the fed-in gas is condensed and in the vessel 4 is separated and thence fed through the line 5 to the vessel 6 which is a collector of the process condensates.

The gas separated from the condensates is sent through the line 7 to the absorption column 8, in which it is contacted, in counterflow relationship, with a selective solvent, the latter being fed-in through the line 9.

From the bottom of 8 and through the line 10, the solvent enriched with carbon dioxide is discharged, to be sent to the regeneration column 3, whereas from the head of the column 8, through the line 11, the gas stripped of carbon dioxide is obtained.

In the column 3 the solvent is regenerated and there is obtained from the bottom, through the pump 12 and the line 9, the regenerated solvent, whereas, from the head, and through the line 13, a stream is obtained which is substantially composed by carbon dioxide, which latter can be used in the urea synthesis.

Conversely, in the tank 14 are collected all the process condensates as obtained from the urea synthesis.

These condensates are sent through the line 15, after having been heated in the heat exchangers 16 and 17, to the hydrolyzer 18. From the latter, through the line 19, the waters substantially free of urea values, are fed to the column 20, from the top of which and through the condenser 21 and the line 22, a head fraction is obtained, which is enriched with ammonia and carbon dioxide, these latter being susceptible of being reused in the urea synthesis. From the bottom, conversely, there are obtained the process condensates which, through the line 23, are combined at 6 with the process condensates coming from 4. The combined condensates are fed by the pump 24 to a filtration system 25, in which the solids which are possibly present in suspension are stripped: in the separator system 26 and boiler 27 saturated or superheated steam is produced which, through the line 28, is recycled to the steam-reforming stage. As an alternative the waters combined at 6 can be subjected to an additional expansion and stripping so as to complete the removal of the dissolved gases.

As a rule, however, the direct use of such waters is no problem for the steam generator boilers or the steam-reforming reactors, either. The substance of the invention is not altered in any wise if the place where the stream 5 and 23 are combined is, rather than the vessel 6, any point downstream of the latter such as the line 28 and the vessel 26.

The following practical embodiment shows the advantage which can be obtained from the method according to the invention.

EXAMPLE

A urea-production line having an output of 1,000 metric tons daily of ammonia and 1,740 metric tons daily of urea produces the following condensates as reported in TABLE 1.

TABLE 1

|  | Installation for ammonia | Installation for urea | Total |
| --- | --- | --- | --- |
| Rate of flow, kilograms hourly | 50,000 | 33,000 | 83,000 |
| Temperature, °C. | 150 | 135 | 144 |
| Composition % by weight NH$_3$ | 0.08 | 0.004 | 0.05 |
| CH$_3$OH | 0.15 | — | 0.09 |
| CO$_2$ | 0.07 | 0.005 | 0.04 |
| N$_2$ + H$_2$ | traces | — | traces |
| urea | — | 0.015 | 0.01 |
| H$_2$O | 99.7 | 99.976 | 99.81 |

TABLE 1-continued

|  | Installation for ammonia | Installation for urea | Total |
| --- | --- | --- | --- |
| TOTALS | 100.00 | 100.00 | 100.00 |

The combined waters are fed to the boiler for the production of saturated or superheated steam, 82,840 kilograms hourly of steam being thus obtained which are sent to the steam-reforming step.

Inasmuch as the steam demanded by a steam-reforming installation providing an output of ammonia of 1,000 tons an hour is 93,000 kilograms an hour, there is an economy in the fresh steam demand as high as 89%.

The advantages which can be obtained are thus related to the reduced consumption of water for generating steam of about 82,000 liters an hour, those related to the diminished hourly consumption of heat for the production of steam, correspondingly to the sensible heat recovered from the condensates which amount to about 7.8 million of kilocalories hourly and the reduced consumption of electric power of about 30 kilowatt, hourly. Concurrently, the discharge from the installation, each hour, of 41 kilograms of ammonia, 75 kilograms of methanol and 5 kilograms of urea is avoided.

We claim:

1. In a multistage process for producing urea, including a first stage for the production, from a gaseous mixture of hydrogen, nitrogen, CO$_2$ and H$_2$O from steam reforming, of a mixture of hydrogen and nitrogen for use as a feed in the synthesis of ammonia, in which water in said gaseous mixture is condensed as a first aqueous condensate, said first aqueous condensate is separated from the gases therein and CO$_2$ is then separated from said gases as a feed in urea synthesis, a second stage for the synthesis of ammonia from the mixture of hydrogen and nitrogen, and a third stage for the synthesis of urea from the ammonia and CO$_2$ with the production of H$_2$O, the improvement consisting essentially of condensing the H$_2$O, produced in said third stage as a second aqueous condensate, mixing said first and second aqueous condensates to form a combined aqueous condensate containing impurities including ammonia, urea, carbon dioxide, nitrogen, methanol, and hydrogen, passing said combined aqueous condensate through a filter adapted to remove solids therefrom, feeding said filtered combined aqueous condensate containing said impurities to a boiler so that steam is produced therefrom, and then utilizing said steam in the steam reforming in said first stage.

2. The process of claim 1 wherein said combined aqueous condensate also contains trace amounts of metals.

* * * * *